United States Patent [19]

Uren et al.

[11] Patent Number: 4,721,673
[45] Date of Patent: Jan. 26, 1988

[54] RECOVERY AND ACTIVATION PROCESS FOR MICROBIALLY PRODUCED CALF PROCHYMOSIN

[75] Inventors: Jack R. Uren, Gaithersburg; Douglas E. Robinson, Frederick, both of Md.; Carl J. Scandella, Oakland, Calif.

[73] Assignee: Genex Corporation, Gaithersburg, Md.

[21] Appl. No.: 587,029

[22] Filed: Mar. 6, 1984

Related U.S. Application Data

[63] Continuation-in-part of Ser. No. 528,421, Sep. 1, 1983, abandoned.

[51] Int. Cl.$^4$ ............................ C12N 9/00; C12N 9/52
[52] U.S. Cl. ...................................... 435/183; 435/68; 435/70; 435/220; 435/226; 435/816
[58] Field of Search ............... 260/112 R, 112.5 R, 260/; 935/19-21, 49, 51, 82, 60, 73, 47; 435/41, 68-71, 87-92, 106, 170, 172.1, 172.3, 183, 188, 184, 219-226, 814-816, 849, 243, 253, 259; 210/632, 634, 639, 645, 647, 648; 530/412, 422

[56] References Cited

U.S. PATENT DOCUMENTS

| | | | |
|---|---|---|---|
| 2,376,848 | 5/1945 | Hankinson | 435/226 |
| 2,506,877 | 5/1950 | Keil | 435/226 |
| 3,151,039 | 9/1964 | Arima | 435/226 |
| 3,616,233 | 10/1971 | Schleich | 435/226 |
| 4,136,201 | 1/1979 | Feldman | 435/226 |
| 4,511,502 | 4/1985 | Builder et al. | 260/112 R |
| 4,511,503 | 4/1985 | Olson et al. | 260/112 R |
| 4,512,922 | 4/1985 | Jones et al. | 260/112 R |
| 4,518,526 | 5/1985 | Olson | 260/112R |

FOREIGN PATENT DOCUMENTS

| | | |
|---|---|---|
| 404600 | 6/1982 | Canada . |
| 0057350 | 11/1982 | European Pat. Off. . |
| 0068691 | 1/1983 | European Pat. Off. . |
| EP068691 | 1/1983 | European Pat. Off. . |
| 0073029 | 3/1983 | European Pat. Off. . |
| 0077109 | 4/1983 | European Pat. Off. . |
| 0114507 | 8/1984 | European Pat. Off. . |
| 0116778 | 8/1984 | European Pat. Off. . |
| 0122080 | 10/1984 | European Pat. Off. . |
| 0121775 | 10/1984 | European Pat. Off. . |
| EP122080 | 10/1984 | European Pat. Off. . |
| 0123928 | 11/1984 | European Pat. Off. . |
| GB83/00152 | 12/1983 | PCT Int'l Appl. . |
| WO84/03711 | 9/1984 | PCT Int'l Appl. . |
| WO83/04418 | 12/1984 | PTC Int'l Appl. . |
| 2100737 | 6/1982 | United Kingdom . |
| 8308234 | 3/1983 | United Kingdom . |
| 2138004 | 10/1984 | United Kingdom . |

OTHER PUBLICATIONS

Nishimori, K. et al., Gene 29: 41-49 (7-1984).
Emtage, J. S. et al, Proc. Natl. Acad. Sci., USA (6-1983), 80: 3671-3675.
Lehninger, A. L., *Principle of Biochemistry*, Worth Publishers Inc. (1982), pp. 177-179.
Foltmann, B. et al., J. Biological Chemistry, 254(17): 8447-8456 (9-1974).
Asato, N. et al, Biochemical Journal, 167: 429-434 (1977).
Penefsky, H. S. et al, Methods in Enzymology XXII: 204-212 (1971), Academic Press, N.Y., W. J. Jakoby, ed.
Nishimori, K. et al, Gene 19: 337-344 (10-1982).
Foltmann, B., Methods in Enzymology, XIX: 421-436 (1970).

*Primary Examiner*—Margaret Moskowitz
*Attorney, Agent, or Firm*—Saidman, Sterne, Kessler & Goldstein

[57] ABSTRACT

A process for the extraction and activation of microbially produced bovine prochymosin is disclosed.

7 Claims, No Drawings

RECOVERY AND ACTIVATION PROCESS FOR MICROBIALLY PRODUCED CALF PROCHYMOSIN

This application is a continuation-in-part of copending U.S. application Ser. No. 528,421 filed Sept. 1, 1983, abandoned.

BACKGROUND OF THE INVENTION

Chymosin (also called rennin E.C. 3.2.23.4) is an enzyme isolated from the fourth stomach of the calf. It is valued for its ability to produce milk curds by catalyzing the hydrolysis of kappa-casein to para-kappa-casein which, in the presence of calcium ion, precipitates as the insoluble curd calcium paracaseinate. After removal of the whey, the curd is processed to make various types of cheeses. Although several proteolytic enzymes will clot milk, the best cheeses have been produced from milk clotted with preparations rich in chymosin. The availability of chymosin—and ultimately its price—depends upon the demand for veal, since the production of chymosin diminishes, and the production of pepsin increases, as the animal matures and is weaned. Enzymes similar to chymosin have been extracted from microorganisms fungi, especially *Mucor mehei*, but the curd and, ultimately, the taste of the cheese are different. The superiority of chymosin for cheese making is probably related to the highly specific manner in which it attacks its substrate, kappa-casein.

Bovine calf chymosin exists as two isozymes (designated A and B), which can be resolved by DEAE-cellulose chromatography of the crystalline enzyme. Isozyme B, which may be catalytically less efficient than isozyme A, is the more abundant form in tissue extracts. Bovine calf chymosin isozyme B has been sequenced, and isozyme A has been partially sequenced, to reveal only one amino acid difference at residue 290 (glycine in B and aspartic acid in A) (see Foltmann, B. et al., *J. Biol. Chem.*, 254: 844–8457 [1976]).

Chymosin is synthesized within the cells of the stomach lining in a precursor form known as preprochymosin. The "pre" portion of preprochymosin is a sequence of amino acids located at the amino terminus. These amino acids comprise a signal peptide which appears to be involved in the transport of the protein to the cell wall for secretion into the periplasmic space. The signal peptide is cleaved at the cell wall and the enzyme is secreted as prochymosin. Prochymosin is a zymogen containing 365 amino acids (40,477 Daltons). Prochymosin is converted to chymosin by the specific removal of 42N-terminal amino acids. The conversion of prochymosin to chymosin is favored by the low pH environment of the stomach.

Particular attention has been directed to studying the conversion of prochymosin to chymosin. Prochymosin was first reported by Hammersten in 1872 (Hammersten, O., *Upsala Laekarefoeren.* Foerh., 8, 63 (1872)). It is stable at neutral and alkaline pH and has been isolated by several methods.

Foltmann and coworkers have studied the conversion of natural prochymosin to chymosin (Pedersen, V. B. and Foltmann, B., *Eur. J. Biochem.* 55, 95 (1975)); (Foltmann, B. et al., *Proc. Nat. Acad. Sci.* (U.S.) 74, 2321 (1977)). (Pedersen, V. B., Christensen, K. A. and Foltmann, B., *J. Biochem.* 94, 573 (1979); Foltmann, B., *C. R. Trav. Lab.* Carlsberg, 35, 143 (1966)). They proposed that at pH2, an intermolecular proteolysis occurs which cleaves the prochymosin at the Phe-Leu[27–28] bond, to produce an active form, "pseudochymosin", which converts to chymosin at pH 4.0 or greater by intramolecular proteolysis. Others have postulated an intramolecular reaction for the generation of pseudochymosin (Al-Janaki et al., *J. Biol. Chem.*, 247, 46 28 (1972)).

With the advent of recombinant DNA technology, it has become possible to produce prochymosin by the expression, in a transformed microorganism, of cDNA encoding the amino acid sequence of prochymosin under the control of a promoter and regulatory sequence. Copending, commonly assigned U.S. patent application Ser. No. 511,766, abandoned, filed July 7, 1983, describes a method of producing chymosin which involves expressing a DNA sequence encoding a fusion protein. The fusion protein comprises an amino-terminal fragment of a microbial protein normally associated with the promoter sequence (e.g., the β subunit of tryptophan synthetase) fused to "activatable prochymosin". The activatable prochymosin comprises the amino acid sequence of "mature" chymosin together with a sufficient portion of its prosequence (at least about 15 amino acid residues) such that the product can undergo post translational autocatalytic cleavage to produce active chymosin. In addition to a portion of the prosequence, the prochymosin fusion product can contain part or all of the signal peptide of preprochymosin and/or a short linker sequence of amino acids, the latter being situated between the amino-terminal fragment of the microbial protein and the amino acid residues of prochymosin (or preprochymosin). The linker sequence in the expressed protein results from the translation of a synthetic DNA linker sequence which serves to fuse the DNA sequence encoding the microbial protein fragment to the DNA sequence encoding prochymosin (or preprochymosin) in the expression vector and to keep the reading frames of the sequences encoding the two segments in phase.

The expression product, i.e., the prochymosin fusion protein, forms an insoluble precipitate within the cells. After cell lysis, this precipitate is both insoluble in conventional solvents for proteins and incapable of undergoing activation by autocatalytic cleavage to produce mature chymosin. The inability of the expression product to self-activate is believed to be related to improper folding of the expressed protein, which in turn is related to the unnatural environment of the microbial host in which it is expressed. Accordingly, there is needed a method of recovering and activating microbially produced prochymosin.

SUMMARY OF THE INVENTION

This invention is based on our discovery that microbially produced bovine prochymosin can be recovered and activated by a process which comprises:

(a) solubilizing the expressed prochymosin in a denaturing solvent;

(b) renaturing the prochymosin by removing or diluting the denaturing agent in the solvent;

(c) activating the renatured prochymosin at low pH to produce active pseudochymosin; and (d) elevating the pH and incubating the pseudochymosin to produce active mature chymosin.

DETAILED DESCRIPTION OF THE INVENTION

The process of the invention provides a method for recovering and activating microbially produced bovine prochymosin. As used herein, the term "microbially produced prochymosin" refers to bovine prochymosin which is produced by expression in a microbial host (e.g., *E. coli*) of exogenous DNA encoding the amino acid sequence of chymosin and at least a sufficient amount of its 42-amino acid prosequence to allow autocatalytic conversion to active mature chymosin following the process described herein. It has been found that at least about the carboxy-terminal 14 amino acids of the prochymosin prosequence are necessary to obtain a marginal level of activation. Preferably at least 20 amino acids of the prosequence are present, most preferably at least 40. If desired, all or a portion of the signal peptide of preprochymosin may also be present. Further, the microbially produced prochymosin which may be subjected to the process of the invention may be in the form of a fusion protein in which the amino acid sequence of prochymosin is fused, at its amino-terminal end to all or a fragment of a microbial protein, such as the $\beta$ subunit of tryptophan synthetase, the expression of which is normally directed by the particular promoter-operator sequence used to direct the expression of the prochymosin. When the prochymosin is expressed as a fusion protein, a linker sequence of amino acids may also be present. The linker sequence serves to join the amino acid sequence of the microbial protein to the amino acid sequence of the prochymosin. Since expression of the microbially produced prochymosin is initiated by the presence of an ATG sequence, which is translated at the ribosome as methionine, the microbially produced prochymosin will normally have methionine as its first amino acid residue.

Microbially produced bovine prochymosin suitable for use in the process of the invention is described in detail in U.S. patent application Ser. No. 511,766, abandoned the disclosure of which is incorporated herein by reference. In particular, there is described a microbially produced prochymosin which is produced by expression, in a transformant, of a DNA sequence, under the control of a trp promoter, encoding an amino-terminal fragment of the subunit of tryptophan synthetase fused to the $\beta$ amino acid sequence of prochymosin (less its first two amino acids). The sequence encoding the first 27 amino acids of the $\beta$ subunit of tryptophan synthetase is linked to the prochymosin-encoding sequence through a linker sequence which encodes the residues

PRO-SER-MET-ALA-GLY-ARG-SER-PHE-ASP-GLN

An *E. coli* strain (GX 1670) transformed with a plasmid containing this DNA sequence, pGX 2231, has been deposited with NRRL, Peoria, Ill., with accession No. B-15571. Another plasmid suitable for use in the microbial production of prochymosin is pGX1049, which contains the fused trp B fragment/prochymosin gene under the control of a hybrid promoter formed from portions of the early leftward and rightward promoters of phage $\lambda$. An *E. coli* strain (GX1214/pGX1049) transformed with plasmid pGX1049 has been deposited with The American Type Culture Collection, Rockville, Md. with accession number ATCC No. 67392. The hybrid promoter is repressed by the cI857 temperature sensitive repressor protein.

When the microbially produced bovine prochymosin is expressed in a non-secreting host such as *E. coli*, the cells must be lysed to release the bovine prochymosin prior to subjecting the prochymosin to the process of our invention. The cells containing the expressed bovine prochymosin are first harvested from the fermentation medium in which the cells are grown, normally by centrifugation. The cells are then lysed to release the bovine prochymosin. When working with small cultures of non-secreting host cells, we prefer to employ a French press to lyse the cells. Other conventional methods for cell lysis may be employed, however, such as the use of mechanical homogenizers or enzymatic or chemical means. The prochymosin, along with other insoluble cellular protein and debris, may be removed from the soluble molecules by any means known to those skilled in the art, as for example, by centrifugation at 10,000 xg.

The microbially produced bovine prochymosin, which is contained in the centrifugation pellet, can be employed as the starting material in the process of our invention. The microbially produced bovine prochymosin is solubilized in a denaturing solvent. A denaturing solvent is a solvent which is known to solubilize proteins and denature them. Examples of suitable denaturing solvents include strong bases such as NaOH, or other solubilizers such as urea or guanidine. The pH of the solution is preferably about 12.0 or greater if a base such as NaOH is employed. Alternatively, 8M urea or 7M guanidine can be employed. The solution can be produced by resuspending the centrifugation pellet containing the microbially produced bovine prochymosin in a dilute sodium hydroxide solution to the desired protein concentration. While it is preferred to employ sodium hydroxide in the preparation of the solution, other commercially available solubilizers, such as guanidine and urea, can also be employed.

The denatured microbially produced bovine prochymosin is then renatured, either by removing or diluting the denaturing agent, this is preferably achieved by diluting the solution with deionized water and adjusting to a pH of about 8.5 to 10.5. The solution is incubated at this pH in the presence of a buffer such as glycine. Incubation is carried out at a temperature which promotes renaturation. The incubation temperature generally ranges from about 4° C. to 37° C. Incubation is continued until the microbially produced bovine prochymosin has reconformed so that it is capable of undergoing conversion to active chymosin. The time of incubation will depend somewhat upon the temperature at which the incubation is carried out. We have found that incubation for 48 hours at 4° C. effectively restores activity to microbially produced bovine prochymosin.

If urea or guanidine is employed as the denaturing agent, renaturation is preferably effected by dialyzing the solution, using known dialysis techniques, to remove the urea or guanidine.

We have found that denaturation by NaOH concentrations equal to or greater than 0.01M, 8M urea or 6M guanidine HCl for periods of time in excess of a few minutes inhibits subsequent renaturation of prochymosin to a form capable of undergoing conversion to active chymosin. The amount of time at which the prochymosin can be held under denaturing conditions without significantly affecting renaturation depends on the concentration of denaturing solvent and the temperature. When denaturation is effected by addition of 0.1M NaOH at room temperature, we have found that dilution of the NaOH to renature the prochymosin is preferably carried out immediately after denaturing conditions are achieved.

In a preferred embodiment of the invention, the centrifugation pellet is resuspended in a chilled solution of a chelating agent such as tetrasodium ethylenediamine tetraacetic acid (about 10 mM) at a protein concentration of about 10 mg/ml or greater. The resulting slurry is solubilized and denatured by the addition of NaOH to a final concentration of about 0.1M. The solubilization product, which is highly viscous, is immediately diluted 10 fold with deionized water and the pH adjusted to 10.0 by the addition of glycine. Final glycine concentrations can be from 10 mM to 50 mM. Renaturation is then performed by incubating at about 24° C. for 20 to 24 hours.

Following renaturation, the microbially produced bovine prochymosin, having assumed the configuration of the naturally produced material, can be converted to active chymosin by techniques which serve to cleave the presequences of amino acids from the sequence of mature active chymosin. While this can be achieved using exogenous proteolytic enzymes, we prefer to convert the renatured prochymosin to chymosin by lowering the pH of the solution containing the prochymosin to below about 2.5. The pH is then adjusted to about 4.0 to 7.0, preferably about 6.0, which causes the pseudochymosin to convert to active mature chymosin. In the practice of the invention, we have carried out the conversion to pseudochymosin by lowering the pH of the solution to about 2.0 by the addition of a non-oxidizing acid, such as hydrochloric acid, and allowing the solution to stand at 4° C.

Since active pseudochymosin is highly soluble at pH 2.0, extraneous proteins from the host cell in which the prochymosin was expressed can be conveniently salted out by adjusting the solution to 0.2–0.3M sodium chloride, followed by centrifugation at 10,000 xg. to precipitate the extraneous proteins.

The active pseudochymosin is present in the final solution in low concentration. Concentrated and more highly purified solutions can be obtained by adsorption of the chymosin on a cation exchange resin with pKa of less than 2.5. The resin may be conveniently washed with pH 2 buffer to remove non-adsorbed contaminating protein and then extracted with a buffer solution with a pH of 6.0 to remove adsorbed chymosin. At pH 6.0, the pseudochymosin undergoes proteolysis to active mature chymosin.

Alternatively, following the conversion of prochymosin to pseudochymosin by acidification to pH 2.5 or below, the pseudochymosin may be purified and converted to chymosin by a simple titration to pH 6.0 to 6.5 with sodium phosphate. This titration results in the precipitation of extraneous proteins that can be removed by centrifugation at 10,000 xg. or less. The chymosin containing supernatant from the centrifugation can be concentrated to final form by: adsorption to an anion exchange resin such as DEAE cellulose (Wattman DE-52) followed by elution with 0.5M NaCl in 50 mM sodium phosphate bufer at pH 6.0 to 6.5; precipitation by ammonium sulfate (60% saturation) or saturated sodium chloride followed by resolubilization in sodium acaetate or sodium phosphate buffer, pH 5.5 to 6.5, or ultrafiltration with a 10,000 nominal molecular weight cutoff.

The mature chymosin is stable when refrigerated in pH 6.0 buffer, and may be formulated with stabilizers, coloring agents, etc. or it may be lyophilized to produce a dry powder. The enzyme thus produced may be employed as any conventional rennet extracted from calf stomach, e.g., in cheese making.

EXAMPLE I

Chymosin recovery from pGX2231

*E. coli* transformed with the plasmid pGX2231 was grown in 8 liters of LB broth containing 100 μg/ml ampicillin. The plasmid contains an *E. coli* trp promoter-operator sequence, a sequence encoding a ribosome binding site, an initiation signal, and a DNA sequence, operably linked to the promoter, which encodes a 27-amino acid amino-terminal fragment of the β subunit of tryptophan synthetase fused to prochymosin (less the first two amino acids) through the sequence Pro-Ser-Met-Ala-Gly-Arg-Ser-Phe-Asp-Gln. Growth was followed by measurement of the absorbance at 560 nm. The cells were harvested when the $A_{560}$ reached 2, followed by centrifugation at $10,000 \times G$. Gross wet weight of the cells was 27.3 grams. The cells were resuspended in 80 ml of deionized water and lysed in a French press at 18,000 psi. The lysate was immediately centrifuged at approximately $10,000 \times G$ and the supernate discarded.

The pellet was extracted with 1600 ml of 0.01N sodium hydroxide, and titrated to a pH of 12 to solubilize the prochymosin fusion protein. The solution was then diluted to 4 liters with deionized water. Glycine (15.2 grams) was added as a buffer and the solution was titrated to pH 9.5 with 0.1N hydrochloric acid. The solution was allowed to stand for 48 hours at 4° C. to allow renaturation of the prochymosin fusion protein. The solution was then titrated with hydrochloric acid to pH 2, and allowed to stand for four hours to allow conversion of prochymosin fusion protein to chymosin. Sodium chloride (70.13 grams) was added and the suspension centrifuged at $10,000 \times G$. The supernate containing chymosin was decanted and diluted to 6 liters with deionized water. An ion exchange resin with a pKa near 2.0 (Whatman SE 53) was equilibrated with 0.05M glycine, pH 2.5, and suspended in the diluted supernate. The suspension was agitated for 30 minutes, allowed to stand overnight and the supernate was decanted. The resin, containing adsorbed chymosin, was resuspended in 100 ml of cold 0.05M phosphoric acid. After centrifugation, the supernate was discarded and the resin resuspended in a minimal amount of 0.05M monobasic sodium phosphate, and titrated to pH 6 to desorb the chymosin. The suspension was shaken and then centrifuged at $14,500 \times G$. The supernate (I) was collected and the resin resuspended in 0.05M monobasic sodium phosphate (pH 6) including 0.9M sodium chloride to desorb additional chymosin. After shaking, the suspension was centrifuged and the supernate (II) collected.

Supernates I and II were tested for chymosin activity using the method described below. Supernate I was determined to contain 7.5 units of chymosin; supernate (II) had 1.9 units of chymosin.

Chymosin activity was assayed by its ability to precipitate Kappa-casein in an acidic environment. Dilutions of the enzyme in 50 mM sodium acetate, 10 mM EDTA, pH 5.5 are incubated at room temperature for 24 hours with 2 mg/ml Kappa-casein purified from either whole milk or dehydrated milk, Zittle, C. A. and Caster, S. H. *J. Dairy Sci.*, 46: 1183–1188 (1963). The chymosin activity is quantitated by comparison of the lowest sample dilution yielding paracaseinate precipitate with the lowest dilution of standard single strength calf rennet causing precipitation. 1 unit=1 ml the activity of of single strength calf rennet.

EXAMPLE II

Chymosin recovery from pGX1049

*E. coli* strain GX1214 transformed with the plasmid pGX1049 was grown in 9 liters of defined medium at 32° C. Expression of chymosin was induced by a temperature shift to 42° C. for one hour. Following the 42° C. temperature period, the broth was cooled to 39° C. and maintained at that temperature for 2 hours. At that point, the cells were harvested. Growth was followed by measurement of absorbance at 540 nm. When the A540 reached 8.0, the cells were induced. Cells were harvested by concentration to about 2 liters with 0.45μ Durapore membranes in a Pellicon (Millipore) then centrifuged at 8,000 rpm ($\approx$9,000$\times$g) for 30 minutes. The resulting 209.1 gram cell pellet (wet weight) was resuspended in 836 ml. of deionized water. The cells were lysed by two passes through a Manton-Gaulin cell disrupter at an operating pressure of 9,000 p.s.i. The lysate was centrifuged at about 9,000$\times$g for 20 minutes and the supernatant was discarded. The pellet was resuspended in approximately 1 liter of deionized water, then centrifuged at about 9,000$\times$g for 20 minutes and the supernatant discarded.

The pellet was resuspended in 126 ml. of chilled 10 mM ethylenediaminetetracetic acid tetrasodium salt. The material was then solubilized by addition of 14 ml. of 1 $\underline{N}$ NaOH with stirring. The solubilized material was immediately diluted with 1120 ml. of deionized water (room temperature) and neutralized to approximately pH 10.0 by the addition of 140 ml. of 0.1M glycine. The material was centrifuged at about 10,000$\times$g for 30 minutes to remove cell debris. The material was allowed to stand at room temperature for approximately 67 hours, then titrated to pH 2.0 by addition of 1.0 $\underline{N}$ HCl. After three days under refrigeration to allow conversion to active pseudochymosin, 955 ml. of the pH 2.0 solution was brought pH 6.5 by the rapid addition of approximately 85.5 ml. of 0.5M Na$_2$HPO$_4$. The sample was stirred for 30 minutes, then centrifuged at approximately 10,000$\times$g for 20 minutes. The supernatant was collected and stored under refrigeration. To increase the yield, the centrifugation pellet was redissolved in 500 ml. of 0.05M glycine, pH 2.0 and refrigerated overnight. The pH 2.0 solution was centrifuged at approximately 9,000$\times$g for 10 minutes. The supernatant was adjusted to pH 6.5 by rapid addition of 0.5M Na$_2$HPO$_4$ and stirred for 30 minutes, then centrifuged. The supernatant was combined with the previous pH 6.5 supernatant to give a final volume of 1760 ml. The pH 6.5 supernatant (1755 ml.) was brought to 60% saturation with 647.6 grams of ammonium sulfate under refrigeration to precipitate the active chymosin. Chymosin activity of the pH 2.0 (prechymosin) solution, the pH 6.5 (chymosin) solution and the (NH$_4$)$_2$SO$_4$ pellet was measured by milk clotting activity, with 1 unit defined as the activity of 1 ml. of single strength rennet. The results are presented below.

| Sample | Volume (mL.) | Chymosin Activity (m Unit/ml.) | Total Activity (Units) |
|---|---|---|---|
| pH 2.0 (pseudochymosin) | 955 | 78.2 | 74.5 |
| pH 6.5 (chymosin) | 1,760 | 36.2 | 63.7 |
| (NH$_4$)$_2$SO$_4$ pellet | 422 | 143.6 | 60.6 |

What is claimed is:

1. A process for converting microbially produced bovine prochymosin into a renatured form of prochymosin which is capable of conversion to pseudochymosin at a pH of about 2.0, which process comprises:
   (a) solubilizing a preparation of microbially produced bovine prochymosin in a solution of a base, said solution having a pH of at least 12.0;
   (b) reducing the pH of said solution to between 8.5 and 10.5; and
   (c) maintaining said preparation of microbially produced bovine prochymosin in said solution, thereby converting said microbially produced bovine prochymosin into a renatured form of prochymosin which is capable of conversion to pseudochymosin at a pH of about 2.0.

2. Th process of claim 1, wherein the base is NaOH.

3. The process of claim 1, wherein the prochymosin is solubilized in a sodium hydroxide solution having a sodium hydroxide concentration of at least 0.01M.

4. A process for converting microbially produced bovine prochymosin into pseudochymosin, which process comprises:
   (a) solubilizing a preparation of microbially produced bovine prochymosin in a solution of a base, said solution having a pH of at least 12.0;
   (b) reducing the pH of said solution to between 8.5 and 10.5;
   (c) maintaining said preparation of microbially produced bovine prochymosin in said solution, thereby converting said preparation of microbially produced bovine prochymosin into a renatured form of prochymosin which is capable of conversion of pseudochymosin at a pH of about 2.0; and
   (d) reducing the pH of said solution to below 2.5, thereby converting said microbially produced bovine prochymosin into pseudochymosin.

5. The process of claim 4 wherein the base is NaOH.

6. The process of claim 4, wherein the prochymosin is solubilized in a sodium hydroxide solution having a sodium hydroxide concentration of at least 0.01M.

7. The process of claim 4, wherein the pH of the renatured prochymosin solution is reduced to about 2.0.

* * * * *